(12) United States Patent
Smith

(10) Patent No.: US 10,111,778 B2
(45) Date of Patent: Oct. 30, 2018

(54) BSS-ONLY MULTI-SPORT LASER PROBE

(71) Applicant: Novartis AG, Basel (CH)

(72) Inventor: Ronald T. Smith, Irvine, CA (US)

(73) Assignee: Novartis AG, Basel (CH)

( * ) Notice: Subject to any disclaimer, the term of this patent is extended or adjusted under 35 U.S.C. 154(b) by 363 days.

(21) Appl. No.: 14/576,459

(22) Filed: Dec. 19, 2014

(65) Prior Publication Data

US 2016/0175143 A1 Jun. 23, 2016

(51) Int. Cl.
| | | |
|---|---|---|
| A61F 9/008 | (2006.01) | |
| G02B 23/06 | (2006.01) | |
| G02B 7/02 | (2006.01) | |
| G02B 6/00 | (2006.01) | |
| A61B 18/20 | (2006.01) | |

(52) U.S. Cl.
CPC .......... *A61F 9/008* (2013.01); *A61F 9/0084* (2013.01); *A61F 9/00825* (2013.01); *G02B 6/00* (2013.01); *G02B 7/027* (2013.01); *G02B 23/06* (2013.01); *A61B 2018/2005* (2013.01); *A61F 2009/0087* (2013.01); *A61F 2009/00848* (2013.01); *A61F 2009/00851* (2013.01); *A61F 2009/00872* (2013.01); *A61F 2009/00889* (2013.01); *A61F 2009/00897* (2013.01)

(58) Field of Classification Search
CPC ... A61F 2009/00863; A61B 2018/2005; A61B 18/20
See application file for complete search history.

(56) References Cited

U.S. PATENT DOCUMENTS

| | | | |
|---|---|---|---|
| 5,396,571 | A | 3/1995 | Saadatmanesh et al. |
| 2008/0051770 | A1* | 2/2008 | Scheller .................. A61F 9/008 606/4 |
| 2011/0141759 | A1* | 6/2011 | Smith ..................... A61F 9/008 362/553 |
| 2014/0200566 | A1 | 7/2014 | Smith |

FOREIGN PATENT DOCUMENTS

WO 2014/162268 10/2014

OTHER PUBLICATIONS

PCT International Application No. PCT/US2016/063958, filed Dec. 4, 2015 in International Search Report and Written Opinion dated Mar. 8, 2016, 9 pages.

* cited by examiner

*Primary Examiner* — Michael Kahelin
*Assistant Examiner* — Nathan A Baldwin

(57) ABSTRACT

An optical surgical probe includes a cylindrical cannula; a light guide partially within the cannula to receive a light beam from a light source through a proximal end, to guide the light beam to a distal end of the light guide, and to emit the light beam through the distal end of the light guide; a multi-spot generator at a distal end of the cannula that includes an optical element with a proximal surface to receive the emitted light beam, and a focusing lens, positioned inside the optical element to focus the received light beam into a focused beam, wherein the optical element has a faceted distal surface to split the focused beam into multiple distally emitted beam-components when the optical surgical probe is operated in a fluid with an index of refraction of 1.30-1.40, and to confine the focused beam in the optical surgical probe when the optical surgical probe is operated in air.

16 Claims, 5 Drawing Sheets

BSS-ONLY MULTI-SPORT LASER PROBE

BACKGROUND

Technical Field

This invention relates to an optical surgical probe and, more particularly, to a multi-spot laser surgical probe with a faceted distal surface.

Related Art

Optical surgical probes deliver light to a surgical region for a variety of applications. In some applications, it may be useful to deliver light to multiple spots in the surgical region. For example, in pan-retinal photocoagulation of retinal tissue, an optical surgical probe that is configured to split a single laser or light beam into multiple beams focused to multiple retinal spots can cause photocoagulation at these spots simultaneously. Photocoagulating at n=2, 4, 6 spots simultaneously can reduce the time of the pan-retinal photocoagulation procedure approximately by a factor of 2, 4, or 6.

Various probe designs have been employed to produce multiple beams for a multi-spot pattern. For example, some probes include a diffractive element to divide a single beam into multiple beams corresponding to higher diffractive orders. Such diffractive elements are typically positioned inside the surgical probe, as positioning them at the end of the probe would pose substantial design challenges. However, positioning the diffractive elements away from the end of the probe can limit their functionalities.

Therefore, another class of optical surgical probes split the incoming beams into beam components with a multi-spot generator that includes a faceted surface to split the incoming beam, and possibly a ball lens to focus the split beam components.

For either of these probes, a general challenge for the design of beam splitting probes is to fit them into a sufficiently small cannula at the end of the probe. The leading probes today have 23 Gauge cannulas, i.e. an outer diameter of about 0.650 mm. It is a non-obvious challenge to design the beam splitting elements to fit into these very narrow cannulas.

Finally, since in surgical practice the probes may be operated in a number of ways that differ from the recommended operating procedures, the probes need to be able to operate under a variety of conditions, not only under ideal ones. Such non-ideal conditions may include the probes being operated outside the eye, or being operated while having unplanned residue, including loose tissue, debris or blood blocking parts of the optical paths. Thus, a need persists for optical surgical probes that can produce well-controlled multiple spots at a surgical target region using optical elements that can fit into a narrow cannula at the probe's end, and they can do so under a variety of non-recommended conditions.

SUMMARY

Consistent with some embodiments, an optical surgical probe can include a cylindrical cannula; a light guide partially within the cannula, configured to receive a light beam from a light source through a proximal end, to guide the light beam to a distal end of the light guide, and to emit the light beam through the distal end of the light guide; a multi-spot generator at a distal end of the cannula, the multi-spot generator including an optical element with a proximal surface to receive the emitted light beam, and a focusing lens, positioned inside the optical element to focus the received light beam into a focused beam, wherein the optical element has a faceted distal surface configured to split the focused beam into multiple distally emitted beam-components when the optical surgical probe is operated in a fluid with a fluid index of refraction in the 1.30-1.40 range, and to confine the focused beam within the optical surgical probe when the optical surgical probe is operated in air.

Figure 1:
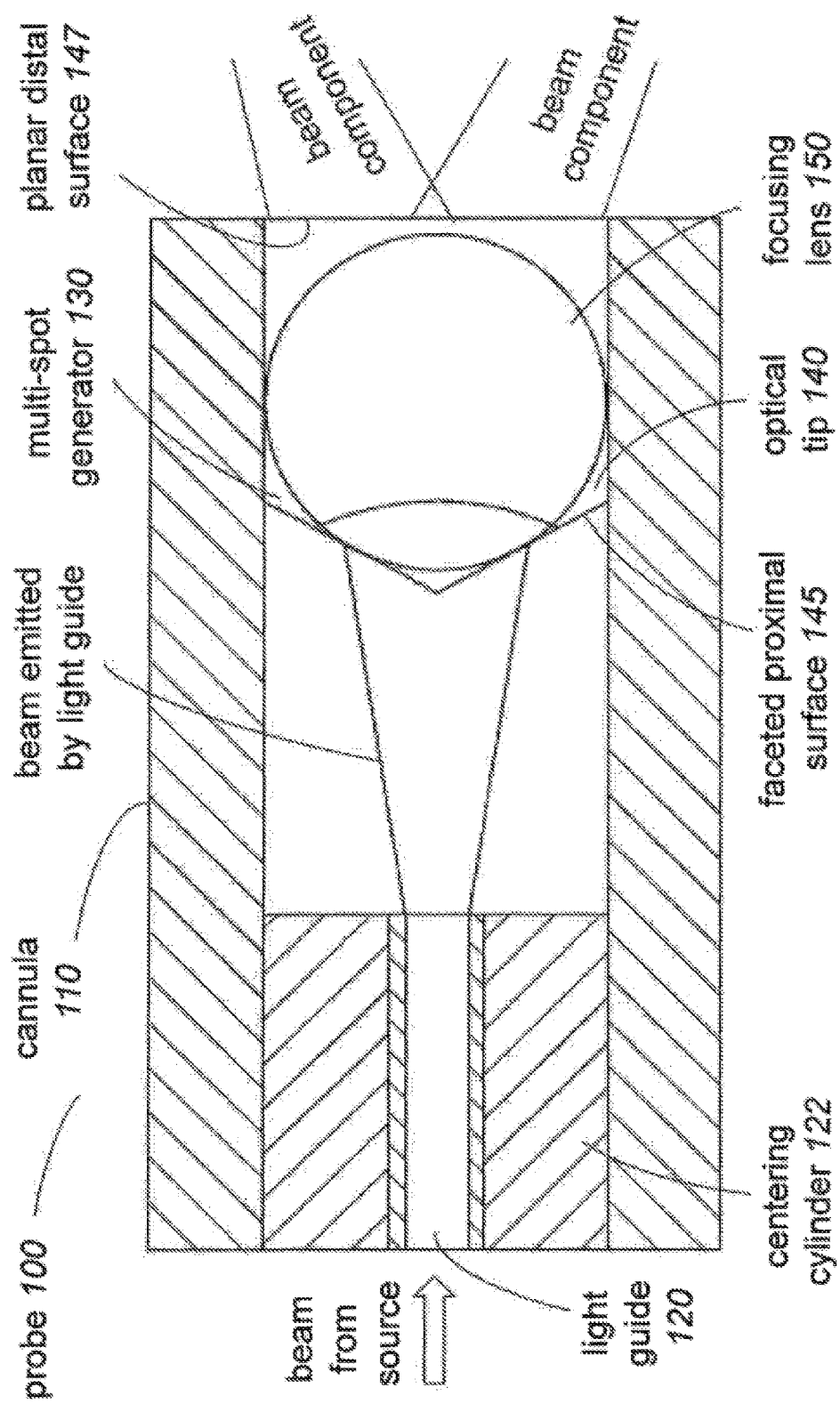
FIG. 1 illustrates an existing multi-spot optical surgical probe.

In the drawings, elements having the same designation have the same or similar functions.

DETAILED DESCRIPTION

As mentioned in the introduction, one of the design challenges for optical surgical probes is that for a variety of reasons, they may be operated in non-recommended ways. Such non-recommended operations can result in undesirable outcomes. While the probes may be designed to perform optimally when inserted into an eye, in some cases the probes may be operated outside the eye, in an ex-ocular operation. Such ex-ocular operation can even be unintended. Further, in some cases, the probes may be operated while the optical path of their light beam is blocked to some degree by unplanned debris, loose tissue, blood, or surgical byproducts getting stuck to the end of the probe. Such blocking may even be hard to detect for an operator, as at some commonly used wavelengths, such as at red wavelengths, the presence of blood at an end of the probe is not easy to see.

A common aspect of these cases is that the non-recommended operation of the probe may raise the temperature of the probe above the optimal design range. In the case of ex-ocular operations, the probe ceases to be cooled by the fluid or vitreous of the posterior chamber of the eye. In the case of partial blocking by debris or blood stuck to the probe's end, the debris may either absorb the light, or can lead to the absorption of the light by the probe itself, both cases leading to overheating. The resulting overheating may in some cases lead to substantial performance deterioration, or partial structural weakening or even detachment of portions of the probe. Therefore, there is a need for optical surgical probes that can avoid overheating even when operated outside the eye, or with beam-blocking debris. As it is widely accepted that optical and thermal properties of the balanced saline solution, or BSS, are reasonably close to the intra-ocular fluids, the above need can be equivalently restated as a need for optical surgical probes that operate properly immersed in a BSS, but stop operating when not immersed in BSS. Such probes can be referred to as "BSS-only" optical surgical probes. In what follows, FIG. 1 and FIG. 2 describe existing optical surgical probes 100, followed by FIGS. 3A-B and FIG. 4 that illustrate BSS-only optical surgical probes 200 according to some embodiments of the present invention that offer improvements over the existing probes 100.

FIG. 1 illustrates a class of existing optical surgical probes. Such optical surgical probe 100 can include a cylindrical cannula 110 and a light guide 120 that is partially positioned within the cannula 110. The light guide 120 can be centered in the cannula 110 by a centering cylinder 122. The light guide 120 can be configured to receive a light beam from a light source through a proximal end, and to emit the light beam through a distal end. The connection to the light source can be fixed or detachable. Detachable probes can be disposable, used only for one patient and procedure. The light beam can be generated by a traditional incoherent light source, a light emitting diode (LED), or any coherent light source, such as a laser source. The wavelength of the light beam can take a wide variety of values. Direct tracking of the surgical procedure can be provided for the surgeon by utilizing a light beam with a wavelength in the visible spectrum approximately in the 400-700 nm range. In some specific cases, the wavelength can be in the 500-600 nm range, such as 532 nm. Some embodiments use the same light guide 120 to guide light at two different wavelengths, such as is the red and green color-range. In some cases, one of the lights can be a low intensity aiming light and the other a higher intensity procedure light, both guided to essentially the same spot in the target region. In an example, a wavelength of the low intensity aiming beam can be 637 nm from a red laser diode, and a wavelength of the high intensity photocoagulation treatment or procedure beam can be 532 nm from a green Nd-YAG laser.

The light guide 120 can be an optical fiber, such as a glass fiber. The light guide can include a fiber with a core diameter of 75-150 microns, with a ferrule coating that is part of a centering cylinder 122. The optical fiber can have a core-cladding-jacket structure. The light beam can be emitted by the light guide 120 with some degree of divergence. The divergent emitted light beam can have, for example, a numerical aperture NA in the range of 0.00-0.30, in some cases in the range of 0.10-0.20.

The light guide 120 can emit the light beam towards a multi-spot generator 130 that is positioned at a distal end of the cannula 110. The multi-spot generator 130 can be positioned at the very end of the cannula 110, its end flush with the cannula's end. In other embodiments, the multi-spot generator can be set back somewhat from the very end of the cannula 110.

Some embodiments of the multi-spot generator 130 can include a cylindrical optical element 140 with a faceted proximal surface 145. Existing optical elements 140 are made of adhesive. The faceted proximal surface 145 can be configured to receive the light beam from the light guide 120, and to split, or to refract the light beam into beam-components. In various embodiments, the faceted proximal surface 145 can have 2, 4, 6 or other suitable number of facets. In some embodiments, the facets can be planar surfaces oblique to the optical axis of the cannula 110. The facets can make an angle with the optical axis in the 10-50 degrees range, in some cases in the 20-40 degrees range. In some embodiments, the facets can be non-planar, curved surfaces.

The multi-spot generator 130 can further include a focusing lens 150 inside the optical element 140. The focusing lens 150 can be fully inside the adhesive optical element 140

The focusing lens 150 can be close to the faceted proximal surface 145, or to a planar distal surface 147 of the optical element 140, but can avoid touching or interrupting these surfaces to avoid disturbing the wavefronts. The focusing lens 150 can be configured to focus the beam-components to multiple spots in an image plane. The focused beam components can be emitted through the distal surface 147 of the optical element 140, as shown. In an image plane, located at 1-8 mm from the distal end of the cannula 110, such as at 4 mm, the beam components can form spots, spaced apart by 0.5-2 mm. Embodiments of the faceted proximal surface 145 with 4 facets create 4 beam components that create 4 spots, for example arranged in a square. A suitably large surgical area can be covered or processed efficiently by placing these spot-squares in a repeating pattern.

Figure 2:
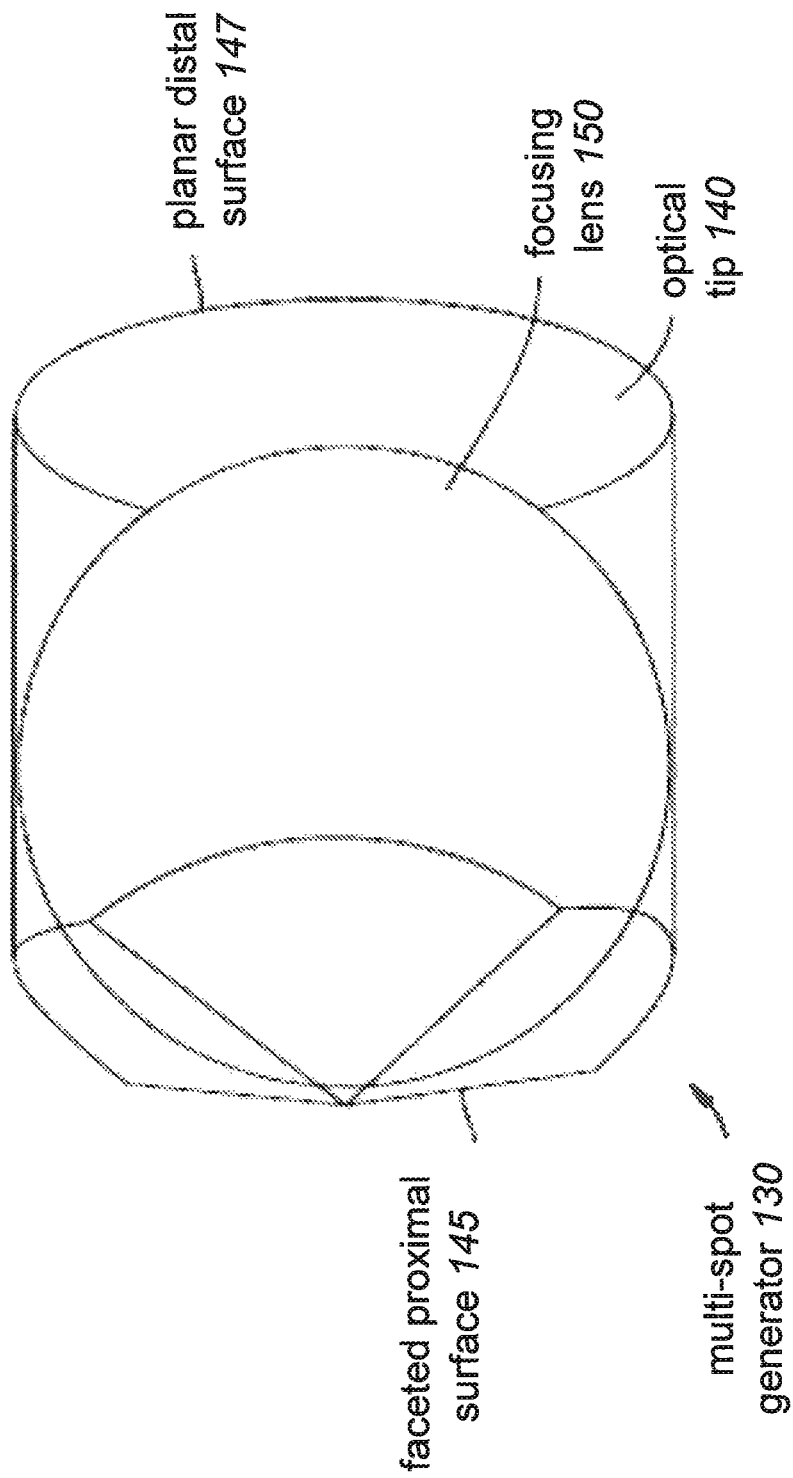
FIG. 2 is a perspective view of the optical surgical probe.

FIG. 2 illustrates an embodiment of the multi-spot generator 130 from a perspective view. As in FIG. 1, this embodiment of the multi-spot generator 130 can include the glass optical element 140 with the faceted proximal surface 145 and the planar distal surface 147. The optical element 140 can further include the focusing lens 150.

The here-described probe 100 works both in BSS as well as in air. The only difference is the angular separation between the spots in air is roughly 1.3-1.5 times the angular separation of the spots in BSS. Therefore, probes of the class of optical surgical probe 100 do not satisfy the above articulated design criteria and do not solve the above stated needs.

Embodiments of the invention offer solutions for the above needs by introducing structural modifications relative to the optical surgical probe 100.

Figure 3A:
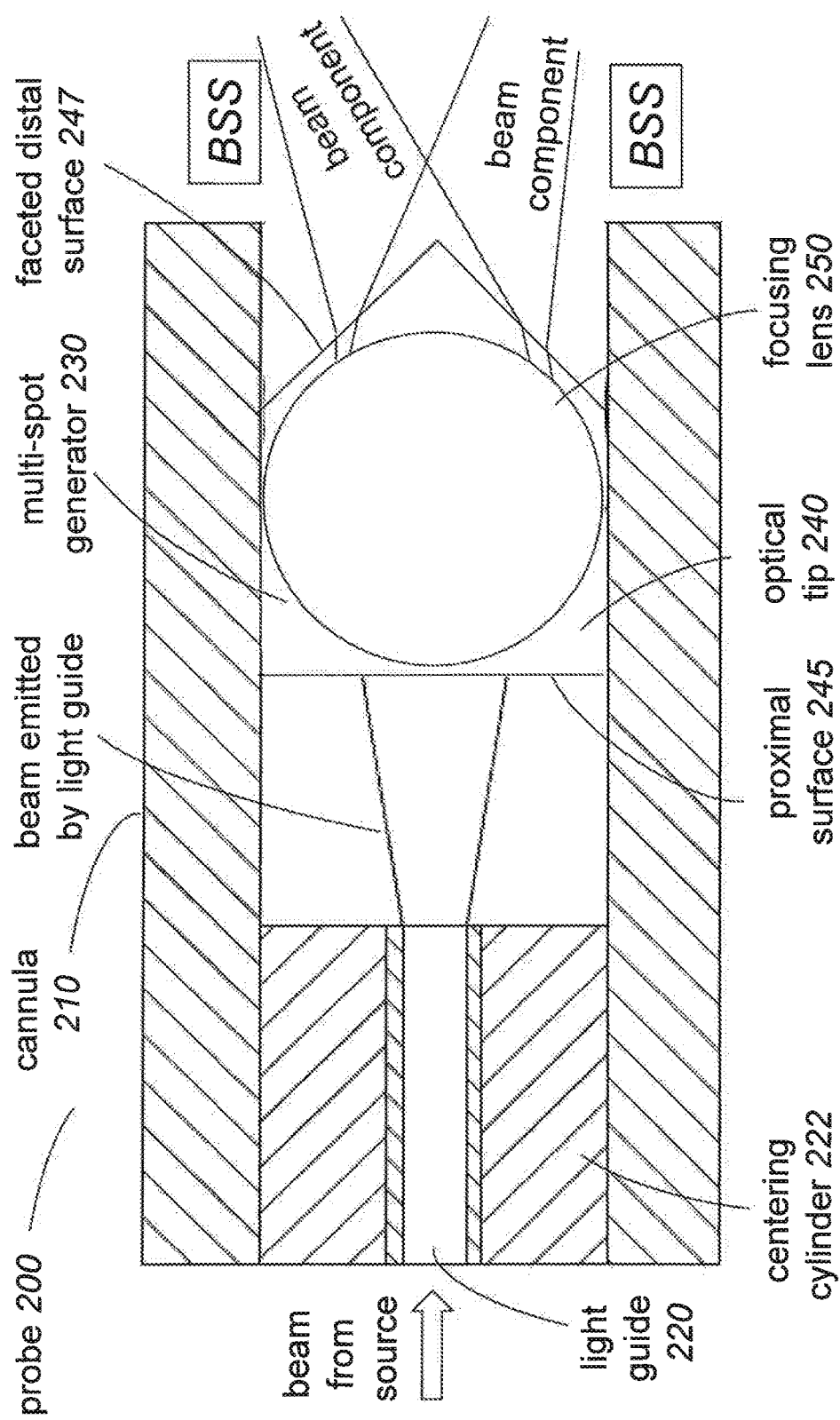
FIGS. 3A-B illustrate multi-spot optical surgical probes operated in a balanced saline solution according to some embodiments of the invention.

FIG. 3A illustrates an optical surgical probe 200 according to embodiments of the present invention. Several elements of the optical surgical probe 200 are analogous to the corresponding elements of the optical surgical probe 100, indicated by analogous labeling, and can have analogous optical and structural characteristics. FIG. 3A shows an optical surgical probe 200 that can include a cylindrical cannula 210, a light guide 220 partially within the cannula 210 to receive a light beam from a light source through a proximal end, to guide the light beam to a distal end of the light guide, and to emit the light beam through the distal end of the light guide 220. As before, the light guide 220 can include an optical fiber, and can be held in place by a centering cylinder 222. The optical surgical probe 200 can further include a multi-spot generator 230 at a distal end of the cannula 210. The multi-spot generator 230 can include an optical element 240 with a proximal surface 245 to receive the emitted light beam from the light guide 220, and a focusing lens 250, positioned inside the optical element 240 to focus the received light beam into a focused beam. In embodiments, the optical element 240 can have a faceted distal surface 247 to split the focused beam into multiple distally emitted beam-components when the optical surgical probe 200 is operated in a fluid with a fluid index of refraction $n_f$ in the 1.30-1.40 range, and to confine the focused beam within the optical surgical probe 200 when the optical surgical probe 200 is operated in air.

In some embodiments, the faceted distal surface 247 can be configured to confine the focused beam without distally emitting beam components when the optical surgical probe 200 is operated in air. Here the lack of distal emission refers to a lack of a substantial distal emission, such as a substantial percentage of the focused beam exiting the faceted distal surface 247. The lack of substantial emissions is not negated by a potential presence of small, residual emissions, where a very low percentage of the focused beam exits the faceted distal surface, caused, e.g., by microscopic residues, scratches and scatterers on the faceted distal surface 247.

In some embodiments of the optical surgical probe 200 the focusing lens 250 is a ball lens, a plano-convex lens, a bi-convex lens, a concave-convex lens, or a meniscus lens.

In some cases the fluid index of refraction $n_f$ can be in the range of 1.35-1.37. In some embodiments, the fluid can be a balanced saline solution. In some embodiments, the focusing lens 250 can be made of sapphire, ruby, zirconia, silica, or glass. In such embodiments, an index of refraction $n_{fl}$ of the focusing lens 250 can be in the range of 1.65-1.85, in some cases in the range of 1.70-1.80. Finally, the optical element 240 can be made of a cured adhesive. An index of refraction $n_{oe}$ of such optical elements 240 can be in the 1.45-1.70 range. In some embodiments, the index of refraction $n_{oe}$ of the optical element 240 can be in the 1.50-1.65 range.

In embodiments with the above material choices for the optical element 240 and for the focusing lens 250, an index of refraction $n_{oe}$ of the optical element 240 can be within 20% of the median or average of the fluid index of refraction $n_f$ and an index of refraction $n_{fl}$ of the focusing lens 250. Such embodiments may be useful to achieve the twin design goals of the optical surgical probe 200 splitting and distally emitting the focused beam into multiple beam-components when immersed in a liquid, such as a BSS, but confining the focused beam without distal emission when the probe is operated in air.

Figure 3B:
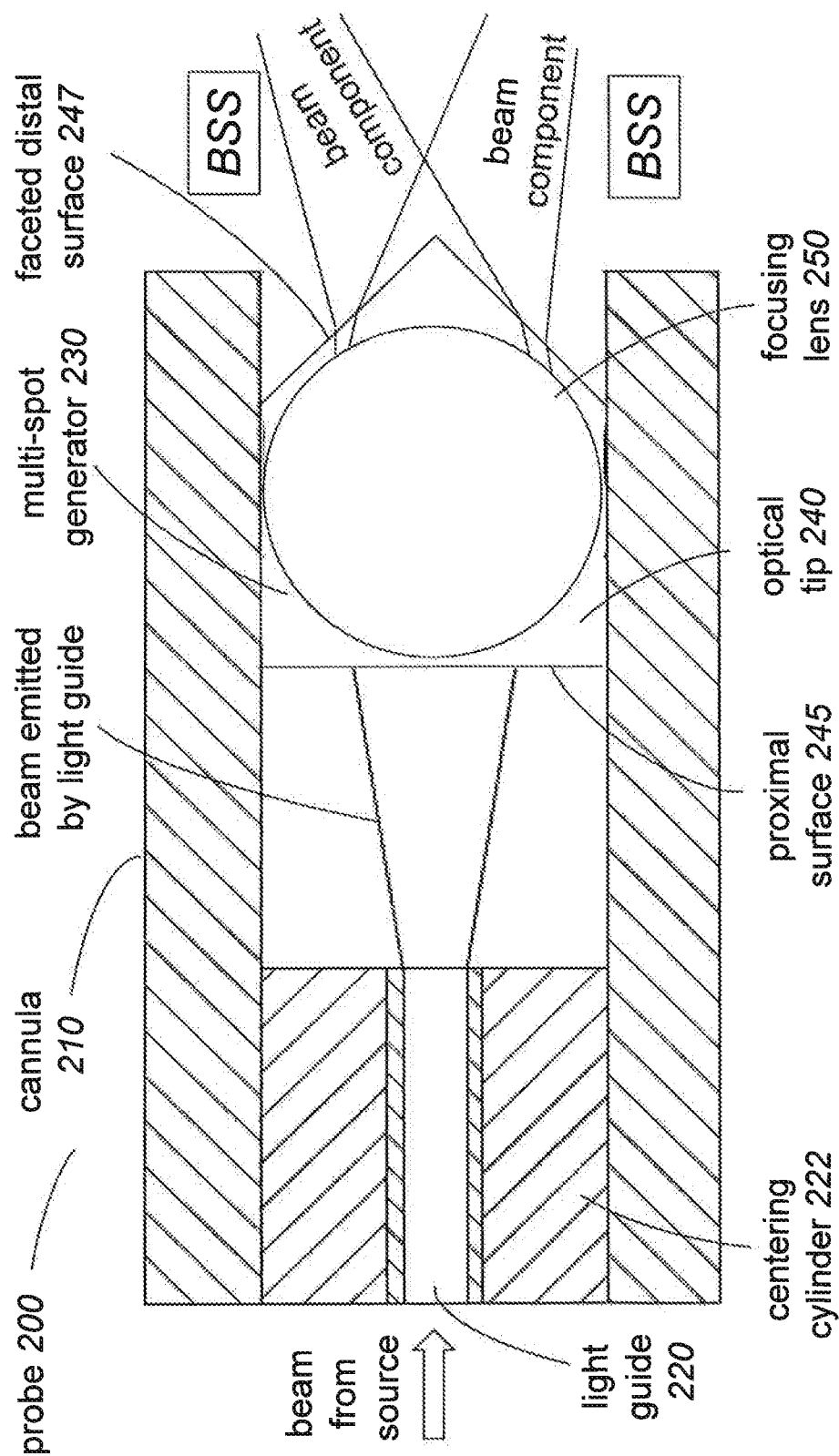

The refractive and reflective performance of the multi-spot generator 230 is impacted not only by the indices of refraction, but also by the orientation or angle of the refractive surfaces, most notably those of the facets of the faceted distal surface 247. In some embodiments, facet-angles of the faceted distal surface 247 and the index of refraction $n_{oe}$ of the optical element 240 can be selected in a combination such that the multi spot generator 230 splits the focused beam into the multiple beam components when inserted into a balanced saline solution, as shown in FIGS. 3A-B. At the same time, the facet-angles of the faceted distal surface 247 and the index of refraction $n_{oe}$ of the optical element 240 can be selected in a combination to cause a total internal reflection, or TIR, of the focused beam to confine the focused beam when the optical surgical probe 200 is operated in air.

Figure 4:
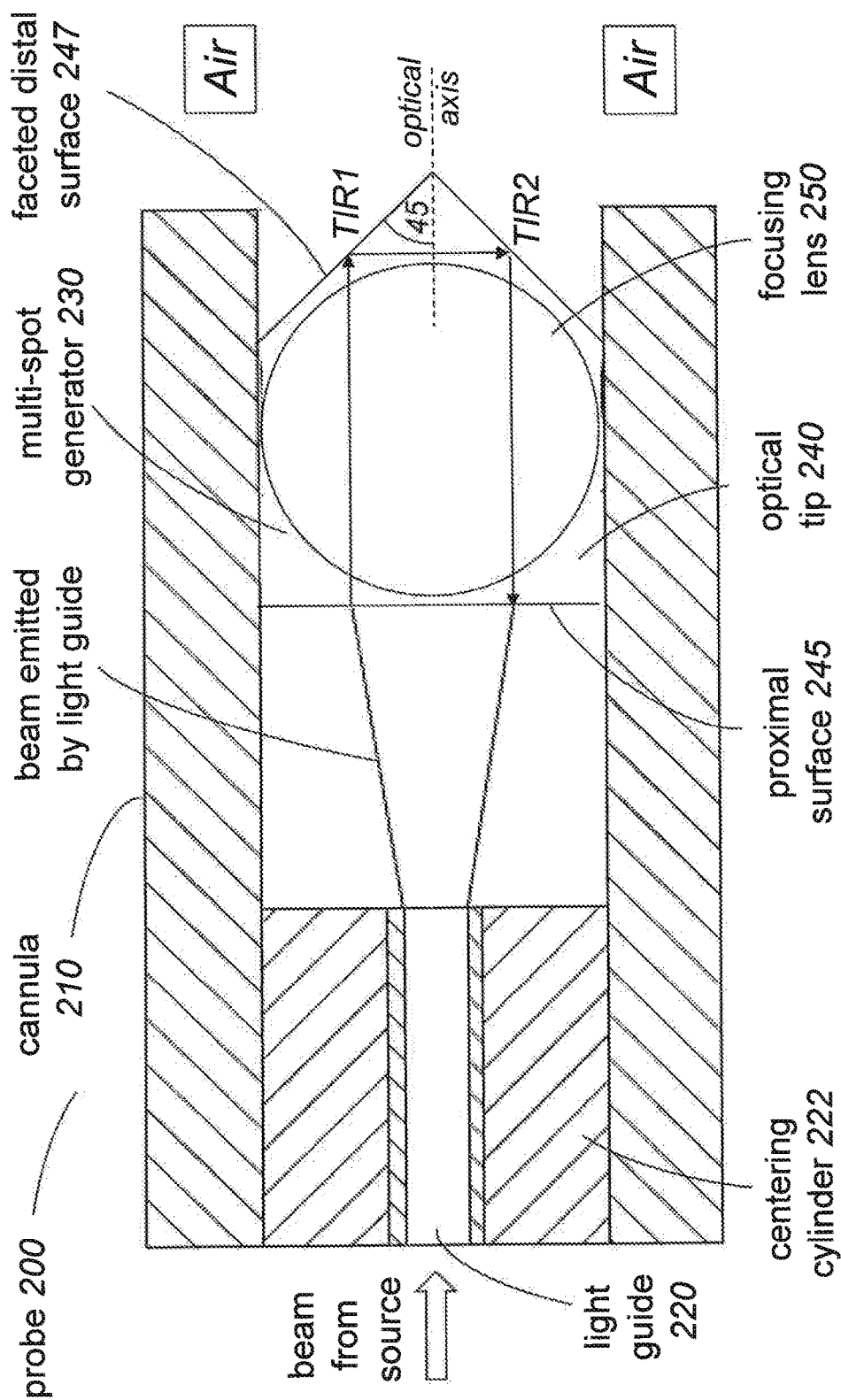
FIG. 4 illustrates a multi-spot optical surgical probe operated in air according to some embodiments of the invention.

FIG. 4 schematically illustrates that in some of these embodiments, the facet-angles of the faceted distal surface 247 and an index of refraction $n_{oe}$ of the optical element 240 can be selected in a combination to confine and reverse the focused beam in a proximal direction through two sequential total internal reflections, TIR1 and TIR 2 when the optical surgical probe 200 is operated in air. The two sequential total internal reflections, suffered at the facets of the faceted distal surface 247, in some embodiments can reverse the focused beam back into the light guide 220. For example, in some embodiments an angle of the facets of the faceted distal surface 247 relative to an optical axis of the optical surgical probe 200 can be in the 20-60 degree range, for example, the angle can be 45 degrees, as shown. In such embodiments, the confined and reversed beam leaves the multi-spot generator 230, propagates away from it in a proximal direction, then can enter the light guide 220 and thus does not deposit its heat in the multi-spot generator 230 or, more generally, at the distal end of the probe 200. Such designs can therefore avoid the undesirable heating of the optical surgical probe 200 very efficiently when not operated or immersed in a BSS.

Probes that do not have the here-described "BSS-only" design of the optical surgical probe 200 often are forced to incorporate additional elements to reduce reflection and thus heating. For example, some designs make use of anti-reflective layers, or anti-reflective nanostructures, or are forced to use less-conventional metals for their cannula that have a particularly high thermal conductivity. Any one of these designs introduces additional steps into the manufacturing process and increases the overall cost of the probe because of the additional structural elements.

In contrast, embodiments of the optical surgical probe 200 make use of only the same elements that are already used in optical surgical probe 100, and only assemble them in a modified manner. The most notable modification is that the optical element 140 is reversed into the optical element 240: the optical element's faceted surface that is the faceted proximal surface 147 in the probe 100 is reversed, forming the faceted distal surface 247 in the probe 200. Since embodiments of the probe 200 reduce local heating without the use of additional structural elements and the corresponding extra manufacturing steps, probes with this "reversed tip" design provide an attractive and economic BSS-only design to reduce heating problems of the optical surgical probes when not immersed in BSS.

FIG. 3A illustrates that in some embodiments, a distal end of the optical element 240 can be proximal to a distal end of the cannula 210. In such embodiments, no part of the optical element 240 extends beyond the distal end of the cannula 210. In such designs the distal end of the optical element 240 is well-shielded from making mechanical contact with external objects, and can thus safely avoid getting sheared, torqued or dislodged from its intended position.

FIG. 3B illustrates that in some embodiments, a distal end of the optical element 240 can be distal to the distal end of the cannula 210. In such embodiments, some portion of the optical element 240 can extend beyond the distal end of the cannula 210. An aspect of such designs is that the recessed space at the end of the probe 200, formed by the optical element 240 and the cannula 210, is smaller than in the designs of FIG. 3A, thus reducing the space where unintended debris, tissue, blood, or surgical byproducts can get stuck, potentially blocking the optical pathway at least partially.

In embodiments of the optical surgical probe 200 the selective reflection or refraction of the light beam can be primarily performed by the faceted distal surface 247, and therefore, the proximal surface 245 of the optical element 240 can be a planar surface.

Embodiments as described herein may provide a multi-spot laser probe having a micro-structured distal surface and a method for manufacturing the same that may reduce an internal reflectance within the laser probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An optical surgical probe comprising:
a cylindrical cannula;
a light guide partially within the cannula, configured
to receive a light beam from a light source through a proximal end,
to guide the light beam to a distal end of the light guide, and
to emit the light beam through the distal end of the light guide;
a multi-spot generator at a distal end of the cannula, the multi-spot generator including
an optical element with a proximal surface to receive the emitted light beam, the optical element having an index of refraction $n_{oe}$ in the range of 1.45-1.70; and
a focusing lens comprising at least one of a ball lens, a plano-convex lens, a bi-convex lens, a concave-convex lens, and a meniscus lens, positioned inside the optical element to focus the received light beam into a focused beam, the focusing lens having an index of refraction $n_{fl}$ in the range of 1.65-1.85, wherein the optical element has a faceted distal surface comprising at least one facet forming an acute facet-angle in the range of 20-60 degrees with respect to a portion of an optical axis centered in the cannula proximal to the faceted distal surface, the at least one facet configured to split the focused beam into multiple distally emitted beam-components when the optical surgical probe is operated in a fluid with a fluid index of refraction in the range of 1.30-1.40, and to confine the focused beam into the optical surgical probe when the optical surgical probe is operated in air.

2. The optical surgical probe of claim 1, wherein:
the fluid index of refraction is in the range of 1.35-1.37.

3. The optical surgical probe of claim 1, wherein:
the fluid is a balanced saline solution.

4. The optical surgical probe of claim 1, wherein:
the faceted distal surface is configured to confine the focused beam without distally emitting beam components when the optical surgical probe is operated in air.

5. The optical surgical probe of claim 1, wherein:
the index of refraction $n_{oe}$ of the optical element is within 20% of the median of the fluid index of refraction $n_f$ and an index of refraction $n_{fl}$ of the focusing lens.

6. The optical surgical probe according to claim 1, wherein:
the index of refraction no, of the optical element is in the 1.50-1.65 range.

7. The optical surgical probe of claim 1, wherein:
the focusing lens comprises at least one of sapphire, ruby, zirconia, silica, and glass.

8. The optical surgical probe of claim 1, wherein:
the optical element comprises a cured adhesive.

9. The optical surgical probe of claim 1, wherein:
the fluid with the fluid index of refraction in the range of 1.30-1.40 is a balanced saline solution.

10. The optical surgical probe of claim 9, wherein:
facet-angles of the faceted distal surface and an index of refraction $n_{oe}$ of the optical element are configured to confine and reverse the focused beam in a proximal direction through two sequential total internal reflections when the optical surgical probe is operated in air.

11. The optical surgical probe of claim 10, wherein:
the two sequential total internal reflections reverse the focused beam back into the light guide.

12. The optical surgical probe of claim 1, wherein:
a distal end of the optical element is proximal to the distal end of the cannula.

13. The optical surgical probe of claim 1, wherein:
a distal end of the optical element is distal to the distal end of the cannula.

14. The optical surgical probe of claim 1, wherein:
the proximal surface of the optical element is a planar surface.

15. An optical surgical probe comprising:
a cylindrical cannula;
a light guide partially within the cannula, configured to
receive a light beam from a light source through a proximal end,
guide the light beam to a distal end of the light guide, and
emit the light beam through the distal end of the light guide;
a multi-spot generator at a distal end of the cannula, the multi-spot generator comprising:
an optical element with a proximal surface to receive the emitted light beam, the optical element having an index of refraction $n_{oe}$ in the range of 1.45-1.70; and
a focusing lens comprising at least one of a ball lens, a plano-convex lens, a bi-convex lens, a concave-convex lens, and a meniscus lens, positioned inside the optical element to focus the received light beam into a focused beam, the focusing lens having an index of refraction $n_{fl}$ in the range of 1.65-1.85;
wherein a distal surface of the optical element comprises at least one facet forming an acute facet-angle in the range of 20-60 degrees with respect to a portion of an optical axis centered in the cannula proximal to the distal surface, the at least one facet-angle configured
to split the focused beam into multiple distally emitted beam-components in response to immersion in a fluid with a fluid index of refraction in the range of 1.30-1.40; and
to confine the focused beam into the optical surgical probe in response to interfacing with air.

16. A method, comprising:
generating, by a light source of an optical surgical probe, a light beam;
receiving the light beam through a proximal end of a light guide situated partially within a cannula of the optical surgical probe;
guiding the light beam to a distal end of the light guide;
emitting the light beam through the distal end of the light guide;
receiving the emitted light beam at a focusing lens positioned inside an optical element of a multi-spot generator situated at a distal end of the cannula, the optical element having an index of refraction $n_{oe}$ in the range of 1.45-1.70;
focusing the emitted light beam into a focused beam by a focusing lens comprising at least one of a ball lens, a plano-convex lens, a bi-convex lens, a concave-convex lens, and a meniscus lens, the focusing lens having an index of refraction $n_{fl}$ in the range of 1.65-1.85;
splitting, by a faceted distal surface of the optical element angled acutely in the range of 20-60 degrees with respect to a portion of an optical axis centered in the cannula proximal to the distal surface, the focused beam into multiple distally emitted beam-components when the optical surgical probe is operated in a fluid with a fluid index of refraction in the range of 1.30-1.40; and
confining, by the faceted distal surface of the optical element, the focused beam into the optical surgical probe when the optical surgical probe is operated in air.

* * * * *